United States Patent [19]
Allen et al.

[11] 4,178,346
[45] Dec. 11, 1979

[54] INCENSE BURNER DEVICE

[76] Inventors: Gerald L. Allen, 6765 Portage Ave.; Craig A. Chapman, 5417 Clem Rd., both of Portage, Ind. 46368

[21] Appl. No.: 916,968

[22] Filed: Jun. 19, 1978

[51] Int. Cl.² .............................................. A61L 9/02
[52] U.S. Cl. ...................................... 422/126; 422/5; 422/306; 431/296
[58] Field of Search .................. 422/126, 5, 239, 306, 422/305; 431/296

[56] References Cited
U.S. PATENT DOCUMENTS

| | | | |
|---|---|---|---|
| 286,572 | 10/1883 | Arzt | 431/296 |
| 414,871 | 11/1889 | Schluster et al. | 431/296 X |
| 589,821 | 9/1897 | Ebeling | 431/296 |
| 2,681,827 | 6/1954 | Racz | 422/123 X |

FOREIGN PATENT DOCUMENTS 153227 7/1904 Fed. Rep. of Germany ........... 431/296

Primary Examiner—Barry S. Richman
Attorney, Agent, or Firm—Walter Leuca

[57] ABSTRACT

An incense burner device adaptable for use in a vehicle such as an automobile. It includes an open ended container for burning incense. A stem extends from the closed end which is removably fitted into the sleeve of a clamp device for supporting the container upright. The clamp device is attachable to a component member of an automobile such as the edge of an ashtray. The ashes of the incense are discharged into the ashtray by removing the container from the sleeve connector and upending it into the ashtray.

2 Claims, 5 Drawing Figures

INCENSE BURNER DEVICE

BACKGROUND OF THE INVENTION

1. Field of the Invention

This invention relates generally to incense burners and more particularly to an incense burner support combination.

2. Description of the Prior Art

The problem that this invention is directed to is providing means for burning incense in a vehicle such as an automobile. There is no prior art device for accomplishing this objective other than the conventional ashtray provided in vehicles. Such ashtrays are unsuited for burning incense.

SUMMARY OF THE INVENTION

This invention includes the provision of a container for burning incense provided with appropriate draft holes to provide for air circulation and for combustion of the burning incense. The incense burner of this invention is removably connected to clamp means for supporting the incense container upright. The incense burner support means of this invention is clamped to a component member of the automobile, preferably the ashtray and more particularly a lip or flange of the ashtray. The incense container is further provided with a stem by which means it connects for support to the clamp means and may be readily removed therefrom so that the incense ashes may be discharged into the ashtray after use. The clamp means member adapted to receive the stem of the container is adjustably movable to support the incense container upright.

Other objects and advantages of my invention will become more apparent after a careful study of the following detailed description taken together with the accompanying drawings which illustrate a preferred embodiment of my invention.

DESCRIPTION OF THE PREFERRED EMBODIMENT

Figure 1:
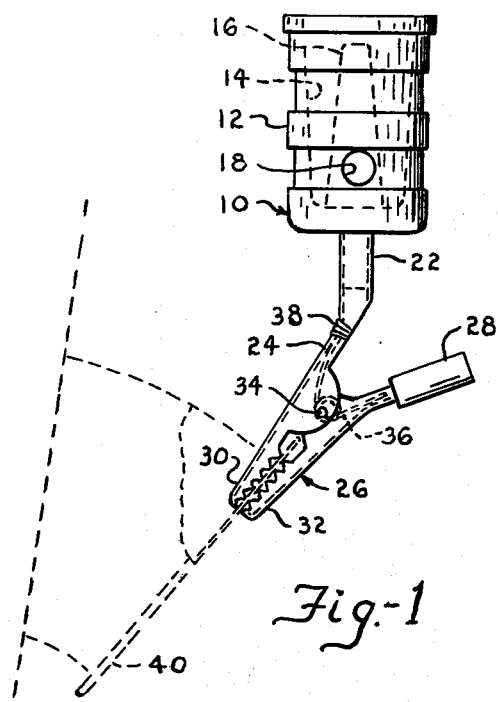
FIG. 1 is an elevational view of this invention shown in operative relation with the ashtray of an automobile.
Figure 2:
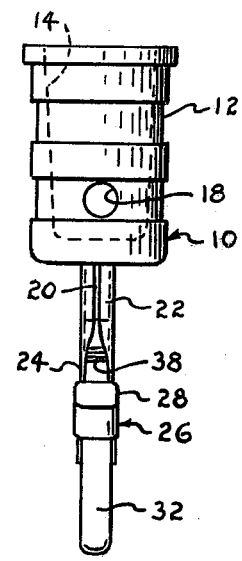
FIG. 2 is a side elevational view.
Figure 3:
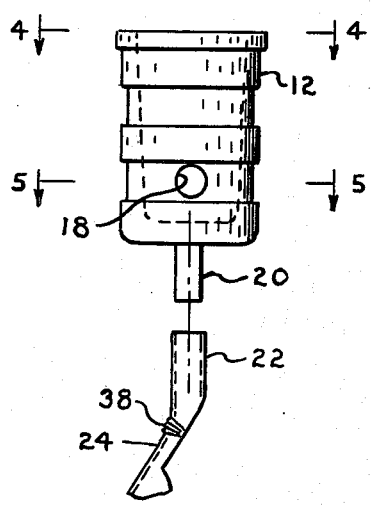
FIG. 3 is an elevational view of the incense burner shown removed from the clip support which is shown in fragment.
Figure 4:
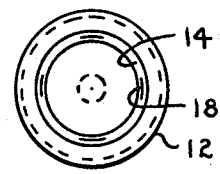
FIG. 4 is a top view taken along lines 4—4 of FIG. 3.
Figure 5:
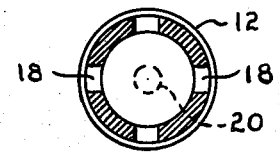
FIG. 5 is a cross sectional view taken along lines 5—5 of FIG. 3.

Referring now more particularly to the drawings wherein is illustrated a preferred embodiment of this invention, numeral 10 designates generally the incense burner of the present invention. It comprises a bottomed container 12 having a hollow 14 for containing therein an incense stick 16 which is shown in dotted lines. Adjacent the bottom of container 12 are a plurality of draft ports 18 spaced around the circumference of the cylindrical container 12 for allowing air to circulate through the container as well as provide air for combustion. Extending from the closed end of container 12 is stem 20 which is inserted in sleeve 22 formed at the distal end of handle 24 of support 26. Handle 28 of support 26 is pivotally connected to handle 24 for scissor-like movement. Clamp ends 30 and 32, of arms 24 and 28, respectively, are normally closed against each other by the bias of a spring member 36 coiled around pivot pin 34.

The portion of handle 24 joining sleeve 22 may be crimped as at 38 to allow manual bending to adjustably position the axis of sleeve 22 with respect to the longitudinal direction of the handle 24.

In the operation of this invention, container 12 is supported upright in sleeve end 22 of handle 24 which is angled in an upright position. After determining the location and position of support 26 by clamping it to the automobile ashtray 40 (shown in dotted lines) or any other desired location, handle 24 is manually bent at crimped portion 38 to adjust sleeve 22 in a vertically upright position for any particular automobile. Consequently, it is not necessary to provide specially formed pivot means for a single application. An incense stick 16 is inserted in hollow 14 of container 12 for burning in the conventional manner. When it is desired to remove the ashes of the incense, the operator merely removes the container 12 by lifting stem 20 out of sleeve 22 and discarding the ashes into ashtray 40 and replace container 12 on support 26.

We claim:

1. A device for handling incense interior of an automobile, comprising:
    a container having an open end, an opposing closed end and circumferentially spaced holes adjacent said closed end;
    an exterior stem axially extending from said closed end;
    lever members pivotally connected together intermediate the opposing distal ends thereof, said lever members having clamp means provided at one pair of corresponding distal ends for coacting against a component member of an automobile for support, and spring means between said lever members for biasing said clamp means together;
    a handle means provided at the opposite distal end of one of said lever members;
    a sleeve means provided at the opposite distal end of the other of said lever members for receiving said stem; and
    means formed on said other of said lever members adjacent said sleeve means for manual deformation to orient said sleeve means to a vertical position.

2. The device of claim 1 wherein said sleeve means is further characterized as having a necked portion formed transversally crimped to facilitate the deformation thereof.

* * * * *